(12) United States Patent
Vedantham et al.

(10) Patent No.: US 7,122,641 B2
(45) Date of Patent: Oct. 17, 2006

(54) METHODS FOR PURIFYING PROTEIN

(75) Inventors: Ganesh Vedantham, Seattle, WA (US); Clayton A. Brooks, III, Bainbridge Island, WA (US); Joanne M. Reeder, Bainbridge Island, WA (US); Andrew M. Goetze, Seattle, MA (US)

(73) Assignee: Immunex Corporation, Thousand Oaks, CA (US)

( * ) Notice: Subject to any disclaimer, the term of this patent is extended or adjusted under 35 U.S.C. 154(b) by 648 days.

(21) Appl. No.: 10/327,495

(22) Filed: Dec. 20, 2002

(65) Prior Publication Data

US 2003/0166869 A1 Sep. 4, 2003

Related U.S. Application Data

(60) Provisional application No. 60/343,363, filed on Dec. 21, 2001, provisional application No. 60/347,189, filed on Jan. 8, 2002, provisional application No. 60/364,272, filed on Mar. 12, 2002.

(51) Int. Cl.
*A61K 39/395* (2006.01)
*C07K 16/00* (2006.01)

(52) U.S. Cl. .................. 530/413; 424/176.1; 530/391.1; 530/415

(58) Field of Classification Search ............. 530/390.1, 530/413, 415; 424/176.1
See application file for complete search history.

(56) References Cited

U.S. PATENT DOCUMENTS

| | | | |
|---|---|---|---|
| 4,745,183 A * | 5/1988 | Engelhorn et al. ........ 530/388.1 |
| 5,095,092 A | 3/1992 | Badziong et al. | |
| 5,115,101 A * | 5/1992 | Bloom et al. ........... 530/388.25 |
| 5,278,284 A | 1/1994 | Lusk et al. | |
| 5,395,760 A | 3/1995 | Smith et al. | |
| 5,610,279 A | 3/1997 | Brockhaus et al. | |
| 5,641,655 A | 6/1997 | Foster et al. | |
| 5,667,787 A | 9/1997 | Jackson et al. | |
| 5,744,587 A | 4/1998 | Alaska et al. | |
| 6,099,830 A | 8/2000 | Kaushansky | |
| 6,121,428 A * | 9/2000 | Blank et al. ................ 530/413 |
| 6,127,526 A | 10/2000 | Blank | |

FOREIGN PATENT DOCUMENTS

| | | |
|---|---|---|
| EP | 0 285 361 A | 10/1988 |
| JP | 63146896 A2 | 6/1988 |
| JP | 2002937 A2 | 1/1990 |
| JP | 3139292 A2 | 6/1991 |
| JP | 3291300 A2 | 12/1991 |
| JP | 4368399 A2 | 12/1992 |
| JP | 5310780 A2 | 11/1993 |
| JP | 6016698 A2 | 1/1994 |
| JP | 8188599 A2 | 7/1996 |

OTHER PUBLICATIONS

Ahmad Z, "Ceramic hydroxyapatite as a polishing step for monoclonal antibody purification," abstract from meeting entitled, "Recovery of Biological Products," held in Whistler, British Columbia, Canada, 1999.
Akerstrom B and Bjorck L, "Protein L: an immunoglobulin light chain-binding bacterial protein characterization of binding and physicochemical properties," *J Biol Chem* 1989 Nov. 25; 264(33):19740-19746.
Apeler H et al., "Expression of natural and synthetic genes encoding herpes simplex virus 1 protease in *Escherichia coli* and purification of the protein," *Eur J Biochem* Aug. 1, 1997; 247(3):890-895.
Aybay C and Imir T, "Development of a rapid, single-step procedure using protein G affinity chromatography to deplete fetal calf serum of its IgG and to isolate murine IgG1 monoclonal antibodies from supernatants of hybridoma cells," *J Immunol Methods* Jan. 13, 2000; 233(1-2):77-81.
Bensinger WI et al., "Clinical trials with Staphylococcal protein A," *J Biol Resp Modif* 1984; 3(3):347-351 (1984).
Bjorck L and Kronvall G, "Purification and some properties of streptococcal protein G, a novel IgG-binding reagent," *J Immunol* Aug. 1984; 133(2):969-974.
Delacroix D and Vaerman JP, "Simple purification of goat IgG1 and IgG2 subclasses by chromatography on protein A-sepharose at various pH," *Mol Immunol* Oct. 1979; 16(10):837-840.
Duhamel RC et al., "The pH-dependent binding of goat IgG1 and IgG2 to protein A-sepharose," *Mol Immunol* Jan. 1980; 17(1):29-36.
Ey PL et al., "Isolation of pure IgG1, IgG2a and IgG2b immunoglobulins from mouse serum using protein A-sepharose," *Immunochemistry* Jul. 1978; 15(7):429-436.
Giovannini R and Freitag R, "Isolation of a recombinant antibody from cell culture supernatant: continuous annular versus batch and expanded-bed chromatography," *Biotechnol Bioeng* Jun. 20, 2001; 73(6):522-529.

(Continued)

*Primary Examiner*—David Saunders
(74) *Attorney, Agent, or Firm*—Rosemary Sweeney

(57) ABSTRACT

A method is provided for separating a protein from one or more other proteins using hydroxyapatite chromatography in which the protein does not bind to hydroxyapatite but the other protein(s) does. In some embodiments, a second protein affixed to a solid support has been used previously to purify the protein by affinity chromatography, and small amounts of the second protein are introduced in the sample during this process. The protein being purified can comprise at least one constant antibody immunoglobulin domain. The second protein can bind to proteins comprising such a domain.

27 Claims, 1 Drawing Sheet

OTHER PUBLICATIONS

Goward CR et al., "Expression and purification of a truncated recombinant streptococcal protein G," *Biochem J* Apr. 1, 1990; 267(1):171-177.

Haino M et al., "Purification of a 60 kDa nuclear localization signal binding protein rat liver nuclear envelopes and characterization of its properties," *J Biochem* (Tokyo) Mar. 1993; 113(3):308-313.

Jungbauer A et al., "Comparison of protein A, protein G and copolymerized hydroxyapatite for the purification of human monoclonal antibodies," *J Chromatogr* 1989; 476:257-268.

Miron T et al., "Characterization of an inhibitor of actin polymerization in vinculin-rich fraction of turkey gizzard smooth muscle," *Eur J Biochem* Dec. 15, 1988; 178(2):543-553.

Poiesi C et al., "Protein A, hydroxyapatite and diethylaminoethyl: evaluation of three procedures for the preparative purification of monoclonal antibodies by high-performance liquid chromatography," *J Chromatogr* 1989; 465:101-111.

Savelkoul HF et al., "Semi-preparative purification and validation of monoclonal antibodies for immunotherapy in mice," *J Immunol Methods* Jun. 3, 1994; 172(1):33-42.

Tarditi, L et al., "Selective high-performance liquid chromatographic purification of bispecific monoclonal antibodies," *J Chromatogr* 1992; 599:13-20.

Tarone G et al., "Purification of the beta subunit of the fibronectin receptor," *Eur J Biochem* Mar. 15, 1988; 172(3):713-718.

Traub A et al., "Purification and properties of the alpha-interferon receptor of human lymphoblastoid (Namalva) cells," *J Biol Chem* Nov. 25, 1984; 259(22):13872-13877.

Vola R et al., "Recombinant proteins L and LG. Two new tools for purification of murine antibody fragments," *Cell Biophys* 1994; 24-25:27-36.

Zola H and Neoh S-H, "Monoclonal antibody purification: choice of method and assessment of purity and yield," *Biotechniques* Sep. 1989; 7(8):802-808.

Federici C et al., "Purification and identification of two putative autolytic sites in human calpain 3 (p. 94) expressed in heterologous systems," *Arch Biochem Biophys* Mar. 1999; 363(2):237-245.

Josic, DJ et al., "Isolation of immunoglobulins and their use in immunoaffinity HPLC," *J Clin Chem Clin Biochem* 1988; 26:559-568.

Ford CHJ et al., "Affinity purification of novel bispecific antibodies recognising carcinoembryonic antigen and doxorubicin," *J Chromatogr B*, 2001; 754:427-435.

Srivastava MD, "Immunomodulatory effects of etanercept (TNFR:Fc) and its use in a patient with Crohn's disease," *Res Commun Mol Pathol Pharmacol* 2001; 109(1-2):125-141.

Strand V, "Recent advances in the treatment of rheumatoid arthritis," *Clin Cornerstone* 1999; 2(2):38-50.

Hodge S et al., "Endogenous tumor necrosis factor-• contributes to lymphoproliferation induced by simian immunodeficiency virus variant, SIVsmmPBj14," *Immunol Lett* 1998; 63:49-51.

Manzke O et al., "Single-step purification of bispecific monoclonal antibodies for immunotherapeutic use by hydrophobic interaction chromatography," *J Immunol Methods* .

* cited by examiner

METHODS FOR PURIFYING PROTEIN

This application claims benefit of three provisional applications, U.S. application Ser. No. 60/343,363, filed Dec. 21, 2001, U.S. application Ser. No. 60/347,189, filed Jan. 8, 2002, and U.S. application Ser. No. 60/364,272, filed Mar. 12, 2002, the disclosures of which are incorporated by reference herein.

FIELD OF THE INVENTION

The invention relates to protein purification, in particular, purification utilizing hydroxyapatite chromatography.

BACKGROUND

Proteins A and G are often employed to purify antibodies by affinity chromatography. See e.g. R. Vola et al. (1994), Cell Biophys. 24–25: 27–36; Aybay and Imir (2000), J. Immunol. Methods 233(1–2): 77–81; Ford et al. (2001), J. Chromatogr. B 754: 427–435. These proteins are useful because they bind to a constant ($F_C$) portion of many different antibodies. Recombinant fusion proteins including an $F_C$ portion of an IgG antibody can be purified using similar methods.

When a protein is produced for pharmacological use, it is important to remove toxic or immunogenic contaminants, such as other proteins. Specifically, Protein A is immunogenic and, in large amounts, potentially toxic. Some Protein A can leach into a sample during affinity chromatography when Protein A affixed to a solid support is used as an adsorbent. See e.g. Bensinger et al. (1984), J. Biol. Response Modif. 3: 347–351; Ventura et al. (1987), Cancer Treat. Rep. 71(4): 411–413 (both of which are incorporated herein in their entirety).

Bispecific monoclonal antibodies have been separated from other antibodies by binding and eluting them from hydroxyapatite subsequent to a pre-purification by affinity chromatography using Protein A affixed to a solid support as an adsorbent. Tarditi et al. (1992), J. Chromatography 599: 13–20; Ford et al. (2001), J. Chromatography B 754: 427–435. Monoclonal antibodies have also been bound and eluted from hydroxyapatite. Ahmad (1999), Ceramic Hydroxyapatite as a Polishing Step for Monoclonal Antibody Purification, Abstract from the Recovery of Biological Products Meeting #9 at Whistler, British Columbia.

The present invention provides a simplified and broadly applicable process for using hydroxyapatite chromatography for purification of antibodies and other proteins.

SUMMARY OF THE INVENTION

Affinity chromatography is a powerful tool for purification of proteins such as antibodies and $F_C$-fusion proteins. However, if the proteins are manufactured for therapeutic use, the presence of other proteins, including a protein used as part of an affinity adsorbent, which can leach into a sample during affinity chromatography, is of concern. In addition, other protein contaminants may also be present in a sample, such as, for example, proteins derived from host cells that produce the protein being purified. The invention provides, among other things, a high yield technique of solving these problems through hydroxyapetite chromatography in a flow-through mode which involves minimal processing.

Accordingly, the invention provides, in one aspect, a method for separating a protein from a second protein comprising subjecting the protein to hydroxyapatite chromatography when (1) the protein has been previously purified by affinity chromatography using the second protein affixed to a solid support as an adsorbent, (2) the second protein can bind to a constant antibody immunoglobulin domain, and (3) the protein does not bind to hydroxyapatite while the second protein does bind to hydroxyapatite under the conditions used. The protein may comprise an $F_C$ portion of an antibody. Optionally, the protein may be TNFR:$F_C$. The second protein may be Protein A or Protein G.

The invention further provides a method for purifying a protein from a sample comprising the protein and at least one protein contaminant comprising subjecting the sample to hydroxyapatite chromatography, wherein the protein is separated from at least one protein contaminant by hydroxyapatite chromatography in a solution in which hydroxyapatite chromatography is performed, wherein the majority of molecules of the protein are recovered in the flow through and wash, wherein the protein has been previously purified by affinity chromatography using a second protein affixed to a solid support as an adsorbent, and wherein the second protein binds to a constant antibody immunoglobulin domain. The second protein may or may not be present at a detectable level in the sample, and the protein can be separated from the second protein by hydroxyapatite chromatography in the solution used. The protein and at least one protein contaminant may have been secreted into a culture medium by cultured animal cells, such as CHO cells. The protein may comprise an $F_C$ portion of an antibody and may, for example, be TNFR:$F_C$ or an antibody. The second protein may be Protein A and Protein G. The solution in which hydroxyapatite chromatography occurs can comprise a sodium phosphate buffer at a concentration between about 5 millimolar and about 50 millimolar, optionally between about 15 millimolar and about 35 millimolar, and can have a pH between about 6.0 and about 8.6.

The invention further provides, in another aspect, a method for separating a recombinant fusion protein from a second protein comprising subjecting the recombinant fusion protein to hydroxyapatite chromatography when (1) the recombinant fusion protein has been previously purified by affinity chromatography using the second protein affixed to a solid support as an adsorbent and (2) the recombinant fusion protein comprises an $F_C$ portion of an antibody and part or all of a non-antibody protein. In one embodiment, the recombinant fusion protein can be TNFR:$F_C$.

In still another aspect, the invention further encompasses a method for separating a recombinant fusion protein from a second protein comprising subjecting the recombinant fusion protein to hydroxyapatite chromatography when (1) the recombinant fusion protein does not bind to hydroxyapatite and the second protein does bind to hydroxyapatite under the conditions used, (2) the recombinant fusion protein has been previously purified by affinity chromatography using the second protein affixed to a solid support as an adsorbent, and (3) the recombinant fusion protein comprises the $F_C$ region of an antibody.

In another embodiment, the invention provides a method for purifying a recombinant fusion protein from sample comprising the recombinant fusion protein and at least one protein contaminant comprising subjecting the sample to hydroxyapatite chromatography, wherein the recombinant fusion protein comprises an $F_C$ portion of an antibody and part or all of a non-antibody protein, and wherein the recombinant fusion protein has been previously purified by affinity chromatography using a second protein affixed to a solid support as an adsorbent. The majority of molecules of the recombinant fusion protein can be recovered in the flow through and wash. The recombinant fusion protein can be TNFR:$F_C$, and the second protein can be Protein A or Protein G. The hydroxyapatite chromatography can be carried out in a solution comprising a sodium phosphate buffer, optionally at a concentration between 5 millimolar and about 50 millimolar or between about 15 millimolar and about 35 millimolar and optionally at a pH between about 6.0 and about 8.6. The recombinant fusion protein and/or at least one protein contaminant can be been secreted into a culture medium by cultured animal cells, optionally CHO cells. In still another aspect of the invention, there is provided a method for separating TNFR:$F_C$ from Protein A comprising subjecting TNFR:$F_C$ to hydroxyapatite chromatography subsequent to purifying TNFR:$F_C$ by affinity chromatography using Protein A affixed to a solid support as an adsorbent.

In a further embodiment, the invention provides a method for purifying TNFR:$F_C$ comprising subjecting a sample comprising TNFR:$F_C$ and at least one protein contaminant to hydroxyapatite chromatography under conditions wherein the majority of molecules of TNFR:$F_C$ are recovered in the flow through and wash.

A further embodiment provides a method for purifying TNFR:$F_c$ comprising subjecting TNFR:$F_C$ to hydroxyapatite chromatography under conditions where TNFR:$F_C$ does not bind to hydroxyapatite, whereby TNFR:$F_C$ is separated from at least one protein contaminant.

The invention further provides, in still another aspect, a method for separating a recombinant fusion protein from host cell proteins comprising loading a sample comprising the recombinant fusion protein onto hydroxyapatite, subjecting the recombinant fusion protein to hydroxyapatite chromatography under conditions where the recombinant fusion protein does not bind to hydroxyapatite, and recovering a sample comprising the recombinant fusion protein in the combined flow through and wash.

In still another aspect, a method is provided for separating a protein from host cell proteins comprising subjecting a sample comprising the protein and at least one host cell protein to hydroxyapatite chromatography, whereby the protein is separated from at least one host cell protein, wherein the protein comprises a constant antibody immunoglobulin domain, wherein the majority of molecules of the protein are recovered in the flow through and wash, and wherein both the protein and the host cell protein have been secreted into a culture medium by cultured animal cells, such as, for example CHO cells. The concentration of the host cell proteins can be less than about 100 parts per million, and the.protein can be TNFR:$F_C$.

The invention also provides a purified preparation of TNFR:$F_C$, wherein the preparation comprises less than 3 parts per million Protein A and less than 100 parts per million host animal cell proteins, optionally less than 2 parts per million Protein A and/or less than 75 parts per million host cell proteins.

DETAILED DESCRIPTION OF THE INVENTION

Definitions

Figure 1:
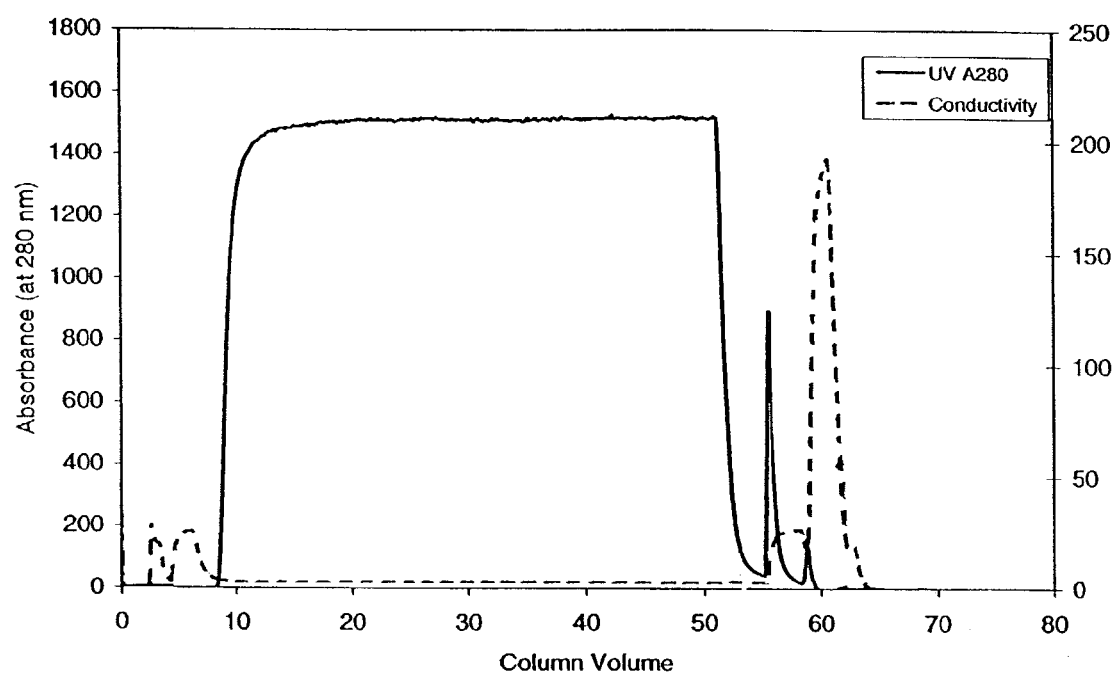
FIG. 1 shows the elution profile of a hydroxyapatite column run in 25 millimolar sodium phosphate, pH 6.8 onto which a sample comprising TNFR: $F_C$ as a majority species was loaded, as described in Example 2.

Adsorbent: An adsorbent is at least one molecule affixed to a solid support or at least one molecule that is, itself, a solid, which is used to perform chromatography.

Affinity chromatography: Affinity chromatography is chromatography that utilizes the specific, reversible interactions between biomolecules, for example, the ability of Protein A to bind to an $F_C$ portion of an IgG antibody, rather than the general properties of a molecule, such as isoelectric point, hydrophobicity, or size, to effect chromatographic separation. In practice, affinity chromatography involves using an adsorbent, such as Protein A affixed to a solid support, to chromatographically separate molecules that bind more or less tightly to the adsorbent. See Ostrove (1990) in *Guide to Protein Purification*, Methods in Enzymology 182: 357–379, which is incorporated herein in its entirety.

Antibody: An antibody is a protein or complex of proteins, each of which comprises at least one variable antibody immunoglobulin domain and at least one constant antibody immunoglobulin domain. Antibodies may be single chain antibodies, dimeric antibodies, or some higher order complex of proteins including, but not limited to, heterodimeric antibodies.

Chromatography: Chromatography is the separation of chemically different molecules in a mixture from one another by percolation of the mixture through an adsorbent, which adsorbs or retains different molecules more or less strongly. Molecules that are least strongly adsorbed to or retained by the adsorbent are released from the adsorbent under conditions where those more strongly adsorbed or retained are not.

Constant antibody immunoglobulin domain: A constant antibody immunoglobulin domain is an immunoglobulin domain that is identical to or substantially similar to a $C_L$, $C_H1$, $C_H2$, $C_H3$, or $C_H4$, domain of human or animal origin. See e.g. Charles A Hasemann and J. Donald Capra, Immunoglobulins: Structure and Function, in William E. Paul, ed., *Fundamental Immunology*, Second Edition, 209, 210–218 (1989), which is incorporated by reference herein in its entirety.

Contaminant: A contaminant is any foreign or objectable molecule, particularly a biological macromolecule such as a DNA, an RNA, or a protein, other than the protein being purified that is present in a sample of a protein being purified. Contaminants include, for example, other proteins from cells that secrete the protein being purified and proteins, such as Protein A, that are part of an adsorbent used for affinity chromatography that may leach into a sample during affinity chromatography.

$F_C$ portion of an antibody: The $F_C$ portion of an antibody includes human or animal immunoglobulin domains $C_H2$ and $C_H3$ or immunoglobulin domains substantially similar to these. For purposes of the invention, the biological activity of an $F_C$ portion of an antibody for the purpose of determining substantial similarity is the ability to be bound by a second protein that binds to naturally-occurring $F_C$ portions of antibodies, such as Protein A or Protein G. For discussion, see Hasemann and Capra, supra, at 212–213.

Host cell proteins: Host cell proteins are proteins encoded by the naturally-occurring genome of a host cell into which DNA encoding a protein that is to be purified is introduced. Host cell proteins may be contaminants of the protein to be purified, the levels of which may be reduced by purification. Host cell proteins can be assayed for by any appropriate method including gel electrophoresis and staining and/or ELISA assay, among others.

Hydroxyapatite chromatography: Hydroxyapatite chromatography is chromatography using ceramic hydroxyapatite as an adsorbent. See e.g. Marina J. Gorbunoff (1990), Protein Chromatography on Hydroxyapatite Columns, in *Guide to Protein Purification*, Murray P. Deutscher, ed., Methods in Enzymology 182: 329–339, which is incorporated herein in its entirety.

IgG antibody: For purposes of the invention, an IgG antibody is an antibody that includes at least one γ type constant immunoglobulin domain. For discussion, see Hasemann and Capra, supra, at 226.

Polypeptide: For the purposes of the invention, "polypeptide" is used interchangeably with "protein."

Protein: A protein is any chain of at least five amino acids linked by peptide bonds.

Protein A: Protein A is a protein originally discovered in the cell wall of *Stapphylococcus* that binds specifically to an $F_C$ portion of IgG antibody. For purposes of the invention, "Protein A" is any protein identical or substantially similar to *Stapphylococcal* Protein A, including commercially available and/or recombinant forms of Protein A. For purposes of the invention, the biological activity of Protein A for the purpose of determining substantial similarity is the capacity to bind to an $F_C$ portion of IgG antibody.

Protein G: Protein G is a protein originally discovered in the cell wall of *Streptococcus* that binds specifically to an $F_C$ portion of an IgG antibody. For purposes of the invention, "Protein G" is any protein identical or substantially similar to Streptococcal Protein G, including commercially available and/or recombinant forms of Protein G. For purposes of the invention, the biological activity of Protein G for the purpose of determining substantial similarity is the capacity to bind to an $F_C$ portion of IgG antibody.

Protein LG: Protein LG is a recombinant fusion protein that binds to IgG antibodies comprising portions of both Protein G (see definition above) and Protein L. Protein L was originally isolated from the cell wall of *Peptostreptococcus*. Protein LG comprises IgG binding domains from both Protein L and G. Vola et al. (1994) Cell. Biophys. 24–25: 27–36, which is incorporated herein in its entirety. For purposes of the invention, "Protein LG" is any protein identical or substantially similar to Protein LG, including commercially available and/or recombinant forms of Protein LG. For purposes of the invention, the biological activity of Protein LG for the purpose of determining substantial similarity is the capacity to bind to an IgG antibody.

Purify: To purify a protein means to reduce the amounts of foreign or objectionable elements, especially biological macromolecules such as proteins or DNA, that may be present in a sample of the protein. The presence of foreign proteins may be assayed by any appropriate method including gel electrophoresis and staining and/or ELISA assay. The presence of DNA may be assayed by any appropriate method including gel electrophoresis and staining and/or assays employing polymerase chain reaction.

Recombinant fusion protein: A recombinant fusion protein is any protein that comprises part or all of two or more proteins that are not fused in their natural state. Examples of such proteins include, but are not limited to, human receptor activator of NF-KappaB fused to an $F_C$ portion of an antibody (huRANK: $F_C$), tunica internal endothelial cell kinase-delta fused to an $F_C$ portion of an antibody (TEKdelta: $F_C$), and tumor necrosis factor receptor fused to an $F_C$ portion of an antibody (TNFR: $F_C$).

Separate: A protein is separated from a second protein in a mixture comprising both proteins when the mixture is subjected to a process such that at least the majority of the molecules of the protein are removed from that portion of the mixture that comprises at least the majority of the molecules of the second protein.

Substantially similar: For purposes of the invention, proteins are substantially similar if they are at least 80%, preferably at least 90% identical to each other in amino acid sequence and maintain or alter in a desirable manner the biological activity of the unaltered protein. Included in amino acids considered identical for the purpose of determining whether proteins are substantially similar are amino acids that are conservative substitutions, unlikely to affect biological activity, including the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and these changes in the reverse. See e.g. Neurath et al., *The Proteins*, Academic Press, New York (1979). The percent identity of two amino sequences can be determined by visual inspection and mathematical calculation, or more preferably, the comparison is done by comparing sequence information using a computer program such as the Genetics Computer Group (GCG; Madison, Wis.) Wisconsin package version 10.0 program, 'GAP' (Devereux et al., 1984, Nucl. Acids Res. 12: 387) or other comparable computer programs. The preferred default parameters for the 'GAP' program includes: (1) the weighted amino acid comparison matrix of Gribskov and Burgess ((1986), *Nucl. Acids Res.* 14: 6745), as described by Schwartz and Dayhoff, eds., *Atlas of Polypeptide Sequence and Structure*, National Biomedical Research Foundation, pp. 353–358 (1979), or other comparable comparison matrices; (2) a penalty of 30 for each gap and an additional penalty of 1 for each symbol in each gap for amino acid sequences; (3) no penalty for end gaps; and (4) no maximum penalty for long gaps. Other programs used by those skilled in the art of sequence comparison can also be used.

TNFR: "TNFR" refers to proteins comprising amino acid sequences that are identical or substantially similar to the sequence of a native mammalian tumor necrosis factor receptor (TNFR). Biological activity for the purpose of determining substantial similarity means the capacity to bind tumor necrosis factor (TNF), to transduce a biological signal initiated by TNF binding to a cell, or to cross-react with anti-TNFR antibodies raised against TNFR from natural (i.e., non-recombinant) sources. A TNFR may be any mammalian TNFR, including murine or human TNFRs. Such TNFRs are described in U.S. Pat. No. 5,395,760, which is incorporated by reference herein in its entirety, and in U.S. Pat. No. 5,610,279, which is incorporated by reference herein in its entirety. A particularly preferred TNFR is that described in U.S. Pat. No. 5,395,760, which has an apparent molecular weight by SDS-PAGE of about 80 kilodaltons in its glycosylated form.

TNFR: $F_C$: TNFR: $F_C$ is a recombinant fusion protein comprising all or part of an extracellular domain of a TNFR fused to an $F_C$ region of an antibody. Such an extracellular domain includes, but is not limited to, amino acid sequences substantially similar to amino acids 1–163, 1–185, or 1–235 of FIG. 2A of U.S. Pat. No. 5,395,760.

Variable antibody immunoglobulin domain: A variable antibody immunoglobulin domain is an immunoglobulin domain that is identical or substantially similar to a $V_L$ or a $V_H$ domain of human or animal origin. For purposes of the invention, the biological activity of a variable antibody immunoglobulin domain for the purpose of determining substantial similarity is antigen binding.

Description of the Method

The process of purifying a protein often involves numerous steps. The present invention encompasses a process for reducing the amount of a second protein in a mixture comprising a protein that is being purified and a second protein, wherein the second protein is introduced during an affinity chromatography step in which the second protein is part of the adsorbent. Removal of such a second protein can be challenging when the isoelectric points of the protein being purified and a complex of the second protein with the protein being purified are close because ion exchange chromatography is unlikely to effect a separation of such proteins. Use of hydroxyapatite makes separation both possible and simple. The methods of the invention also have the added advantage of removing other objectionable matter from the protein. Further, the invention comprises a method for purifying a protein comprising an $F_C$ region of an antibody using hydroxyapatite chromatography under conditions where the protein is recovered in the flow through and wash and at least one protein contaminant is retained on the hydroxyapatite.

In one aspect, the methods of the invention can reduce the amount of a second protein, and/or a complex of the second protein with the protein being purified, which is introduced during affinity chromatography, in a sample that contains the protein being purified. In this aspect, hydroxyapatite chromatography is performed under conditions such that the protein being purified does not bind to hydroxyapatite, but the second protein, and/or a complex of the second protein with the protein being purified, does bind.

The process of the invention can, in some embodiments, also involve at least two steps. First, the protein undergoes a pre-purification step of affinity chromatography using the second protein affixed to a solid support as an adsorbent. Second, hydroxyapatite chromatography is performed under conditions such that the protein does not bind to hydroxyapatite, but the second protein, and/or a complex of the second protein with the protein being purified, does. The entire process of purifying the protein may include other steps before and/or after each of these steps.

Prior to equilibration and chromatography, the hydroxyapatite chromatography medium may be pre-equilibrated in a chosen solution, e.g. a salt and/or buffer solution. Pre-equilibration serves the function of displacing a solution used for regenerating and/or storing the chromatography medium. One of skill in the art will realize that the composition of the pre-equilibration solution depends on the composition of the storage solution and the solution to be used for the subsequent chromatography. Thus, appropriate pre-equilibration solutions may include the same buffer or salt used for performing the chromatography, optionally, at a higher concentration than is used to perform chromatography. Buffers and salts that can be used for chromatography are discussed below. For example, when the solution used to perform chromatography comprises sodium phosphate at a given concentration, pre-equilibration may take place in a in a solution comprising sodium phosphate at a higher concentration. As an illustration of this, if the solution used to perform chromatography comprises sodium phosphate at between about 0.5 millimolar and about 50 millimolar, pre-equilibration may occur in a solution comprising sodium phosphate at concentrations between about 0.2 molar and about 0.5 molar, more preferably in concentrations of sodium phosphate between about 0.3 molar and about 0.4 molar, inclusive.

Before the sample is applied to the column, the hydroxyapatite chromatography medium can be equilibrated in the buffer or salt that will be used to chromatograph the protein. As discussed below, chromatography (and loading of the protein to be purified) can occur in a variety of buffers or salts including sodium, potassium, ammonium, magnesium, calcium, chloride, fluoride, acetate, phosphate, and/or citrate salts and/or Tris buffer. Such buffers or salts can have a pH of at least about 5.5. In some embodiments, equilibration may take place in a solution comprising a Tris or a sodium phosphate buffer. Optionally, the sodium phosphate buffer is at a concentration between about 0.5 millimolar and about 50 millimolar, more preferably at a concentration between about 15 millimolar and 35 millimolar. Preferably, equilibration takes place at a pH of at least about 5.5. Equilibration may take place at pHs between about 6.0 and about 8.6, preferably at pHs between about 6.5 and 7.5. Most preferably, the solution comprises a sodium phosphate buffer at a concentration of about 25 millimolar and at a pH of about 6.8.

Any or all chromatographic steps of the invention can be carried out by any mechanical means. Chromatography may be carried out in a column. The column may be run with or without pressure and from top to bottom or bottom to top. The direction of the flow of fluid in the column may be reversed during the chromatography process. Chromatography may also be carried out using a batch process in which the solid support is separated from the liquid used to load, wash, and elute the sample by any suitable means, including gravity, centrifugation, or filtration. Chromatography may also be carried out by contacting the sample with a filter that adsorbs or retains some molecules in the sample more strongly than others.

The protein can be produced by living host cells that have been genetically engineered to produce the protein. Methods of genetically engineering cells to produce proteins are well known in the art. See e.g. Ausabel et al., eds. (1990), Current Protocols in Molecular Biology (Wiley, New York). Such methods include introducing nucleic acids that encode and allow expression of the protein into living host cells. These host cells can be bacterial cells, fungal cells, or, preferably, animal cells grown in culture. Bacterial host cells include, but are not limited to, *Escherichia coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, BHK, HeLa, Cos, MDCK, 293, 3T3, and WI138. New animal cell lines can be established using methods well know by those skilled in the art (e.g., by transformation, viral infection, and/or selection). Optionally, the protein can be secreted by the host cells into the medium.

Protein concentration of a sample at any stage of purification can be determined by any suitable method. Such methods are well known in the art and include: 1) colorimetric methods such as the Lowry assay, the Bradford assay, the Smith assay, and the colloidal gold assay; 2) methods utilizing the UV absorption properties of proteins; and 3) visual estimation based on stained protein bands on gels relying on comparison with protein standards of known quantity on the same gel. See e.g. Stoschek (1990), Quantitation of Protein, in *Guide to Protein Purification*, Methods in Enzymol. 182: 50–68.

The protein undergoing purification as contemplated by the invention comprises one or more constant antibody immunoglobulin domain(s) and may, but need not, comprise a single or multiple variable antibody immunoglobulin domain(s). It may be a naturally-occurring protein or a recombinant fusion protein. It may comprise an $F_C$ portion of an antibody. It may also comprise a non-antibody protein.

Some proteins specifically contemplated for use with the invention include recombinant fusion proteins comprising one or more constant antibody immunoglobulin domains, optionally an $F_C$ portion of an antibody, and a protein identical to or substantially similar to one of the following proteins: a flt3 ligand (as described in international application no. WO 94/28391, which is incorporated by reference herein in its entirety), a CD40 ligand (as described in U.S. Pat. No. 6,087,329, which is incorporated by reference herein in its entirety), erythropoeitin, thrombopoeitin, calcitonin, Fas ligand, ligand for receptor activator of NF-kappa B (RANKL), tumor necrosis factor (TNF)-related apoptosis-inducing ligand (TRAIL, as described in international application no. WO 97/01633, which is incorporated by reference herein in its entirety), thymic stroma-derived lymphopoietin, granulocyte colony stimulating factor, granulocyte-macrophage colony stimulating factor (GM-CSF, as described in Australian Patent No. 588819, which is incorporated by reference herein in its entirety), mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor (TNF), leukemia inhibitory factor, oncostatin-M, and various ligands for cell surface molecules ELK and Hek (such as the ligands for eph-related kinases or LERKS). Descriptions of proteins that can be purified according to the inventive methods may be found in, for example, *Human Cytokines: Handbook for Basic and Clinical Research, Vol. II* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook* (A. W. Thompson, ed., Academic Press, San Diego, Calif., 1991).

Proteins contemplated by the invention also include recombinant fusion proteins comprising one or more constant antibody immunoglobulin domains, optionally an $F_C$ portion of an antibody, plus a receptor for any of the above-mentioned proteins or proteins substantially similar to such receptors. These receptors include: both forms of TNFR (referred to as p55 and p75), Interleukin-1 receptors types I and II (as described in EP Patent No. 0 460 846, U.S. Pat. No. 4,968,607, and U.S. Pat. No. 5,767,064, which are incorporated by reference herein in their entirety), Interleukin-2 receptor, Interleukin-4 receptor (as described in EP Patent No. 0 367 566 and U.S. Pat. No. 5,856,296, which are incorporated by reference herein in their entirety), Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK, as described in U.S. Pat. No. 6,271,349, which is incorporated by reference herein in its entirety), receptors for TRAIL (including TRAIL receptors 1, 2, 3, and 4), and receptors that comprise death domains, such as Fas or Apoptosis-Inducing Receptor (AIR).

Other proteins that may be purified using the process of the invention include differentiation antigens (referred to as CD proteins) or their ligands or proteins substantially similar to either of these, which are fused to at least one constant antibody immunoglobulin domain, optionally an $F_C$ portion of an antibody. Such antigens are disclosed in *Leukocyte Typing VI* (Proceedings of the VIth International Workshop and Conference, Kishimoto, Kikutani et al., eds., Kobe, Japan, 1996). Similar CD proteins are disclosed in subsequent workshops. Examples of such antigens include CD27, CD30, CD39, CD40, and ligands thereto (CD27 ligand, CD30 ligand, etc.). Several of the CD antigens are members of the TNF receptor family, which also includes 41BB ligand and OX40. The ligands are often members of the TNF family, as are 41BB ligand and OX40 ligand. Accordingly, members of the TNF and TNFR families can also be purified using the present invention.

Enzymatically active proteins or their ligands can also be purified according to the invention. Examples include recombinant fusion proteins comprising at least one constant antibody immunoglobulin domain plus all or part of one of the following proteins or their ligands or a protein substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands.

The method of the invention may also be used to purify antibodies or portions thereof and chimeric antibodies, i.e. antibodies having human constant antibody immunoglobulin domains coupled to one or more murine variable antibody immunoglobulin domain, or fragments thereof. The method of the invention may also be used to purify conjugates comprising an antibody and a cytotoxic or luminescent substance. Such substances include: maytansine derivatives (such as DM1); enterotoxins (such as a *Staphlyococcal* enterotoxin); iodine isotopes (such as iodine-125); technium isotopes (such as Tc-99m); cyanine fluorochromes (such as Cy5.5.18); and ribosome-inactivating proteins (such as bouganin, gelonin, or saporin-S6). Examples of antibodies or antibody/cytotoxin or antibody/luminophore conjugates contemplated by the invention include those that recognize any one or combination of the above-described proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-4, IL-5, IL-8, IL-10, IL-2 receptor, IL-4 receptor, IL-6 receptor, L-13 receptor, IL-18 receptor subunits, PDGF-β, VEGF, TGF, TGF-β2, TGF-β1, EGF receptor, VEGF receptor, C5 complement, IgE, tumor antigen CA 125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, IFN-γ, Respiratory Syncitial Virus, human immunodeficiency virus (HIV), hepatitis B virus (HBV), *Streptococcus mutans*, and *Staphlycoccus aureus*.

The invention may also be used to purify anti-idiotypic antibodies, or substantially similar proteins, including but not limited to anti-idiotypic antibodies against: an antibody targeted to the tumor antigen gp72; an antibody against the ganglioside GD3; or an antibody against the ganglioside GD2.

In affinity chromatography, an adsorbent can comprise a suitable solid support with a second protein affixed to it. A protein sample containing the protein to be purified can be applied to this adsorbent. The adsorbent can be subsequently washed in a solution that does not interfere with the binding of the second protein to the constant antibody immunoglobulin domain of the protein. The protein can thereafter be eluted from the adsorbent with a solution that interferes with the binding of the constant antibody inununoglobulin domain by the second protein.

The second protein is any protein that can bind to a constant antibody immunoglobulin domain, which may, but need not, be a recombinant fusion protein. Optionally, the second protein can be Protein G, Protein LG, or Protein A. The second protein can be affixed to any suitable solid support including: agarose, sepharose, silica, collodion charcoal, sand, and any other suitable material. Such materials are well known in the art. Any suitable method can be used to affix the second protein to the solid support. Methods for affixing proteins to suitable solid supports are well known in the art. See e.g. Ostrove (1990), in *Guide to Protein Purification*, Methods in Enzymology, 182: 357–371. Furthermore, such solid supports already having the second protein affixed are commercially available from a number of manufacturers including BioRad, Merck, Amersham Pharmacia Biotech, and Millipore Corporation.

In an optional step, a protein sample comprising the protein to be purified plus contaminants is loaded onto the adsorbent, which comprises the second protein affixed to a solid support, in a solution comprising a buffer and/or a salt. Suitable buffers include, but are not limited to, phosphate buffers, Tris buffers, acetate buffers, and/or citrate buffers. Suitable salts include, but are not limited to, sodium chloride, potassium chloride, ammonium chloride, sodium acetate, potassium acetate, ammonium acetate, calcium salts, and/or magnesium salts. For example, the solution may comprise Tris at concentrations between about 5 millimolar and 100 millimolar and sodium chloride at concentrations between about 50 millimolar and 250 millimolar. However, other buffers and salts can be used. After loading, the adsorbent, can be washed with more of the same solution. The protein can be eluted using a solution that interferes with the binding of the second protein to the constant antibody immunoglobulin domain. This solution may include a chaotropic agent, such as guanidinium, an agent that can either increase or decrease pH, and/or a salt. This solution may include acetic acid, glycine, or citric acid. Elution may be effected by lowering the pH. For example, the pH can be lowered to about 4.5 or less, typically to between about 3.3 to about 4.0, using a solution comprising citrate or acetate, among other possibilities. Alternatively, the pH can be increased, typically to above about 8.5. Solutions appropriate to effect such elutions may comprise Tris or sodium carbonate, among other possibilities. Other methods of elution are also available. Protocols for such affinity chromatography are well known in the art. See e.g. Miller and Stone (1978), J. Immunol. Methods 24(1–2): 111–125. Conditions for binding and eluting can be easily optimized by those skilled in the art.

In the methods of the invention, the protein is subjected to hydroxyapatite chromatography under conditions in which the protein does not bind to hydroxyapatite but the second protein, and/or a complex of the second protein with the protein, which may be present after affinity chromatography, does. The sample is loaded onto hydroxyapatite and chromatography is performed in a solution comprising a buffer and/or a salt at a pH of greater than about 5.5. Preferably, chromatography can occur in a solution that is the same as or similar to that in which the protein is loaded onto the chromatography medium. Hydroxyapatite chromatography can occur under conditions where the protein and the second protein bind to each other to form a complex or under conditions where they do not. Thus, in the former case, separation of the protein from the second protein can entail separation of the protein from a complex of the second protein with the protein. In the latter case, separation of the protein from the second protein can entail precisely that. Chromatography and loading can occur in a variety of buffers and/or salts including sodium, potassium, ammonium, magnesium, calcium, chloride, fluoride, acetate, phosphate, citrate and/or Tris buffers. Specific examples of such buffers and salts are: Tris, sodium phoshate, potassium phophate, ammonium phosphate, sodium chloride, potassium chloride, ammonium chloride, magnesium chloride, calcium chloride, sodium fluoride, potassium fluoride, ammonium fluoride, calcium fluoride, magnesium fluoride, sodium citrate, potassium citrate, ammonium citrate, magnesium acetate, calcium acetate, sodium acetate, potassium acetate, or ammonium acetate. The pH range is chosen to optimize the chromatography conditions and to retain the desired characteristics of the protein of interest. For most proteins of interest, that may range between about 6.0 and about 8.6, preferably between about 6.5 and about 7.5. However, certain proteins are known to be resistant to pH extremes, and a broader range may be possible. In one embodiment, the loading/chromatography solution comprises a sodium phosphate buffer at a concentration between about 0.5 millimolar and about 50 millimolar, more preferably at a concentration between about 15 millimolar and 35 millimolar sodium phosphate. Optionally, the solution comprises a sodium phosphate buffer at a concentration of about 25 millimolar and at a pH of about 6.8. In another embodiment, the loading solution comprises Tris at a pH between about 6.0 and about 9.0, preferably between about 6.5 and about 8.0.

The flow-through liquid, which comprises the protein being purified, is collected. The selected buffer and/or salt at the selected concentration allows the second protein to bind to hydroxyapatite, while the protein being purified does not. One skilled in the art will be guided by the knowledge in the art in determining which buffer or salt is appropriate for the particular protein being purified. See e.g. Gorbunoff (1990), Protein Chromatography on Hydroxyapatite Columns, in *Guide to Protein Purification*, Methods in Enzymology 182: 329–339; Scopes, *Protein Purification: Principles and Practice*, Third Edition, pp. 173–75, Springer, 1994 (which disclosure is incorporated by reference herein). Moreover, a skilled artisan can easily determine the optimal concentration of the selected buffer or salt to use by, for example, running a gradient of the selected buffer or salt through a hydroxyapatite column to which a sample comprising the protein to be purified and the second protein has been applied. Fractions of the effluent of the column can be collected and analyzed to determine the concentration of buffer or salt at which the protein and the second protein elute. Suitable analyses include, for example, a measurement of electrical conductance with a conductivity meter (to determine the salt concentration in the sample) plus gel electrophoresis or ELISA assay (to determine the identity of the proteins in the sample). Optionally, the hydroxyapatite can be washed with more of the same solution in which the protein sample was loaded, and this wash solution can also be collected and combined with the flow-through liquid.

Subsequent to collection of the flow through and, optionally, the wash, which comprises the protein being purified, proteins that may remain bound to the hydroxyapatite may be released by stripping the chromatography medium using a solution comprising the buffer or salt used for chromatography, but at a higher molarity. Then, the column may be regenerated using a solution that will have the effect of releasing most or all proteins from the chromatography medium and reducing or eliminating any microbial contamination that may be present in the chromatography medium. In one embodiment, such a solution may comprise sodium hydroxide. Other reagents can also be used. Subsequently, the column may be rinsed and stored in a solution that can discourage microbial growth. Such a solution may comprise sodium hydroxide, but other reagents can also be appropriate.

The second protein, a complex of the protein and the second protein, and/or other proteins that may be present in a sample of the protein being purified, can be monitored by any appropriate means. Preferably, the technique should be sensitive enough to detect contaminants in the range between about 2 parts per million (ppm) (calculated as nanograms per milligram of the protein being purified) and 500 ppm. For example, enzyme-linked immunosorbent assay (ELISA), a method well known in the art, may be used to detect contamination of the protein by the second protein. See e.g. Reen (1994), Enzyme-Linked Immunosorbent Assay (ELISA), in *Basic Protein and Peptide Protocols*, Methods Mol. Biol. 32: 461–466, which is incorporated herein by reference in its entirety. In one aspect, hydroxyapatite chromatography may not detectably reduce contamination by a second protein, especially if the material loaded onto hydroxyapatite has levels of the second protein that are close to or below detectable levels. Alternatively, hydroxyapatite chromatography may reduce contamination by a second protein at least about twofold, preferably at least about threefold, more preferably at least about fivefold, still more preferably at least about tenfold, even more preferably at least about fifteenfold, most preferably at least about twentyfold. Preferably, contamination of the protein by the second protein after hydroxyapatite chromatography is not more than about 400 ppm, more preferably not more than about 360 ppm, more preferably not more than about 320 ppm, more preferably not more than about 280 ppm, more preferably not more than about 240 ppm, more preferably not more than about 200 ppm, more preferably not more than about 160 ppm, more preferably not more than about 140 ppm, more preferably not more than about 120 ppm, more preferably not more than about 100 ppm, more preferably not more than about 80 ppm, more preferably not more than about 60 ppm, more preferably not more than about 40 ppm, more preferably not more than about 20 ppm, more preferably not more than about 10 ppm, more preferably not more than about 5 ppm, more preferably not more than about 1 ppm, and most preferably not more than about 0.5 ppm. Contamination by such a second protein can range from undetectable levels to about 5 ppm or from about 5 ppm to about 400 ppm. If a protein is being purified for pharmacological use, one of skill in the art will realize that the preferred level of the second protein can depend on the weekly dose of the protein to be administered per patient, with the aim that the patient will not receive more than a certain amount of a contaminating protein per week. Thus, if the required weekly dose of the protein is decreased, the level of contamination by a second protein may possibly increase.

Similarly, other protein contaminants, including host cell proteins, that may be present in a sample of the protein being purified, can be monitored by any appropriate means, including ELISA assays. In one aspect, contamination of the protein by such other proteins can be reduced after hydroxyapatite chromatography, preferably by at least about twofold, more preferably by at least about threefold, more preferably by at least about fivefold, more preferably by at least about tenfold, more preferably by at least about twentyfold, more preferably by at least about thirtyfold, more preferably by at least about fortyfold, more preferably by at least about fiftyfold, more preferably by at least about sixtyfold, more preferably by at least about seventyfold, more preferably by at least about 80 fold, more preferably by at least about 90 fold, and most preferably by at least about 100 fold. In another aspect, contamination of the protein by such other proteins after hydroxyapatite chromatography is not more than about 10,000 ppm, preferably not more than about 2500 ppm, more preferably not more than about 400 ppm, more preferably not more than about 360 ppm, more preferably not more than about 320 ppm, more preferably not more than about 280 ppm, more preferably not more than about 240 ppm, more preferably not more than about 200 ppm, more preferably not more than about 160 ppm, more preferably not more than about 140 ppm, more preferably not more than about 120 ppm, more preferably not more than about 100 ppm, more preferably not more than about 80 ppm, more preferably not more than about 60 ppm, more preferably not more than about 40 ppm, more preferably not more than about 30 ppm, more preferably not more than about 20 ppm, more preferably not more than about 10 ppm, and most preferably not more than about 5 ppm. Such contamination can range from undetectable levels to about 10 ppm or from about 10 ppm to about 10,000 ppm. If a protein is being purified for pharmacological use, one of skill in the art will realize that the acceptable level of other protein contaminants can depend on the weekly dose of the protein to be administered per patient, as explained above.

The amount of DNA that may be present in a sample of the protein being purified can be determined by any suitable method. For example, one can use an assay utilizing polymerase chain reaction. Optionally, the technique can detect DNA contamination at levels of 10 picograms per milligram of protein and greater. DNA levels can be reduced by hydroxyapatite chromatography, optionally by about twofold, preferably by about fivefold, more preferably by about tenfold, more preferably by about fifteenfold, most preferably by about 20 fold. Optionally, levels of DNA after hydroxyapatite chromatography are less than about 20 picograms per milligram of protein, preferably less than 15 picograms per milligram of protein, more preferably less than 10 picograms per milligram of protein, most preferably less than 5 picograms per milligram of protein.

The following examples are offered by way of illustration and not limitation.

EXAMPLE 1

Reduction in Levels of Protein A in a Sample Comprising TNFR:$F_C$ Using Hydroxyapatite Chromatography This experiment demonstrates that hydroxyapatite chromatography can reduce levels of residual protein A in a protein sample comprising TNFR:$F_C$ that contains a defined amount of protein A, which can form a complex with TNFR:$F_C$.

A column of ceramic hydroxyapatite (Type II, Bio-Rad, 80μ) 18 cm in height and 1.6 cm in internal diameter was pre-equilibrated with two column volumes of 0.4 molar sodium phosphate, pH 6.8 and equilibrated with four column volumes of 25 millimolar sodium phosphate, pH 6.8, which has a conductivity of 2.8 milliSiemens (mS). A protein sample (5.11 milligrams/milliliter) in 668 milliliters of 25 mM sodium phosphate, pH 6.8 comprising TNFR:$F_C$ and protein A (209 ppm) was loaded onto the column. The amount of protein A in the sample was determined using an ELISA assay. The flow-through liquid, containing TNFR:$F_C$, was collected. The column was washed with three column volumes of 25 millimolar sodium phosphate, pH 6.8, and the wash was collected and combined with the flow through. The collected protein in the flow through and wash was sterilized by filtration and stored at 2–8° C. until the next purification step was carried out. Most of the TNFR:$F_C$ loaded is recovered (97%) in the flow-through liquid plus the wash. The amount of protein A in the flow-through plus the wash was measured at 11 ppm. Thereafter, the column was stripped using three column volumes of 0.4 molar sodium phosphate, pH 6.8, regenerated using two column volumes of 1 molar sodium hydroxide, and rinsed with three column volumes of 0.1 molar sodium hydroxide, 10 millimolar sodium phosphate, and stored in the same solution, in which condition it is ready for reuse.

EXAMPLE 2

Reduction in the Levels of Host Cell Proteins in a Sample Comprising TNFR:$F_C$ Using Hydroxyapatite Chromatography The following experiment demonstrates that the levels of host cell proteins in a sample comprising TNFR:$F_C$ can be reduced by hydroxyapatite chromatography.

A column of ceramic hydroxyapatite (Type II, Bio-Rad, 80μ) 10 cm in height and 1.1 cm in internal diameter was pre-equilibrated with two column volumes of 0.3 molar sodium phosphate, pH 6.8 and equilibrated with three column volumes of 25 millimolar sodium phosphate, pH 6.8, which has a conductivity of 2.8 mS. About 1.9 grams of protein in a volume of 382 milliliters of 25 millimolar sodium phosphate, pH 6.8 was loaded onto the column. This sample included TNFR:$F_C$, which comprised the vast majority of the sample, and host cell proteins (545 ppm). The amount of host cell proteins in the sample was determined using ELTSA assays. The flow-through liquid, comprising TNFR:$F_C$, was collected. The column was washed with three column volumes of 25 millimolar sodium phosphate, pH 6.8, and the wash was collected and combined with the flow through. Most of the TNFR:$F_C$ loaded (92%) was recovered in the flow-through liquid plus the wash. The collected TNFR:$F_C$ was sterilized by filtration. The amount of host cell proteins was lowered at least about seventy fold (from 545 ppm to 7 ppm) when compared to the material loaded onto the hydroxyapatite column. Thereafter, the column was stripped using three column volumes of 0.3 molar sodium phosphate, pH 6.8, rinsed with a half column volume of 25 millimolar sodium phosphate, pH 6.8, regenerated using two column volumes of 1 molar sodium hydroxide, rinsed with three column volumes of 0.1 molar sodium hydroxide, 10 millimolar sodium phosphate, and stored in the same solution, in which condition it is ready for reuse.

FIG. 1 shows the absorbance and conductivity profiles of the column. Most of the protein in the sample flows through the column before the increase in conductivity (to about 20 mS) caused by the addition 0.3 molar sodium phosphate, between about 55 and 59 column volumes. The large increase in conductance (to about 200 mS) thereafter corresponds to the addition of 1.0 molar sodium hydroxide to regenerate the column as explained above. Since TNFR:$F_C$ constitutes the vast majority species in the protein sample loaded onto the column, this profile indicates that TNFR:$F_C$ flows through a hydroxyapatite column run in 25 millimolar sodium phosphate, pH 6.8.

EXAMPLE 3

Reduction in Residual Protein A and Other Proteins in a Sample of TNFR:$F_C$ by Ceramic Hydroxyapatite Chromatography The following experiment shows that levels of protein A and other protein contaminants can be simultaneously reduced using hydroxyapatite chromatography.

A column of ceramic hydroxyapatite (Type II, Bio-Rad, 80 μ) 18 cm in height and 1.6 cm in internal diameter was pre-equilibrated with two column volumes of 0.4 M sodium phosphate, pH 6.8 and equilibrated with three column volumes of 25 millimolar sodium phosphate, pH 6.8. About 3.2 grams of protein at about 5 mg/ml in 25 millimolar sodium phosphate comprising TNFR:$F_C$, Protein A, which forms a complex with TNFR:$F_C$ under these conditions, (between about 97 ppm and about 106 ppm), and other process related impurities (PRI; between about 59 ppm and about 67 ppm) was loaded onto the column. The amounts of Protein A and PRI in the sample were determined using ELISA assays. The flow-through liquid, containing TNFR:$F_C$, was collected. The column was washed with three column volumes of 25 millimolar sodium phosphate, pH 6.8, and the wash was collected. Almost all (99–100%) of the TNFR:$F_C$ loaded was recovered in the flow-through liquid plus the wash. The amount of Protein A and PRI in the sample was reduced by 5.3–5.4 fold and 2.8–3.7 fold, respectively, when compared to the material loaded onto the hydroxyapatite column. Thereafter, the column was stripped using five column volumes of 0.4 molar sodium phosphate, pH 6.8, regenerated using two column volumes of 1 M sodium hydroxide, rinsed in three column volumes of 10 millimolar sodium phosphate, pH 6.8, 0.1 M sodium hydroxide, and stored in the same solution, in which condition it is ready for reuse.

The present invention is not to be limited in scope by the specific embodiments described herein, which are intended as single illustrations of individual aspects of the invention, and functionally equivalent methods and components are within the scope of the invention. Indeed, various modifications of the invention besides those described herein will be apparent to those skilled in the art from the foregoing description and accompanying drawings. Such modifications are intended to fall within the scope of the appended claims.

What is claimed is:

1. A method for purifying a protein from a sample comprising the protein and at least one protein contaminant comprising subjecting the sample to hydroxyapatite chromatography in a solution,
   whereby the protein is separated from at least one protein contaminant,
   wherein the majority of molecules of protein are recovered in a the flow though and wash,
   wherein the protein has been previously purified by affinity chromatography using a second protein affixed to a solid support as an adsorbent, and
   wherein the second protein binds specifically to a constant antibody immunoglobulin domain.

2. The method of claim 1, wherein the second protein is present at a detectable level in the sample and wherein the protein is separated from the second protein by hydroxyapatite chromatography in the solution.

3. The method of claim 1, wherein the protein has been secreted into a culture medium by cultured animal cells.

4. The method of claim 3, wherein the animal cells are CHO cells.

5. The method of claim 3, wherein at least one protein contaminant has been secreted into the culture medium by the cultured animal cells.

6. The method of claim 1, wherein the protein comprises an $F_c$ portion of an antibody.

7. The method of claim 6, wherein the protein is TN.FRF$_c$.

8. The method of claim 6, wherein the protein is an antibody.

9. The method of claim 1, wherein the second protein is selected from the group consisting of Protein A and Protein G.

10. The method of claim 1, wherein the solution includes a sodium phosphate buffer at a concentration between about 5 millimolar and about 50 millimolar.

11. The method of claim 1, wherein the solution has a pH between about 6.0 and about 8.6.

12. The method of claim 1 wherein:
   the protein is TNFR:Fc;
   the second protein is Protein A or Protein G; and
   the solution comprises a sodium phosphate buffer at a concentration between about 15 millimolar and about 35 millimolar and has a pH between about 6.5 and about 7.5.

13. A method for purifying a recombinant fusion protein from sample comprising the recombinant fusion protein and at least one protein contaminant comprising subjecting the sample to hydroxyapatite chromatography,
   wherein the majority of molecules of the recombinant fusion protein are recovered in a flow through and wash,
   wherein the recombinant fusion protein comprises one or more constant antibody immunoglobulin domain(s) and part or all of a non-antibody protein,
   wherein the recombinant fusion protein has been previously purified by affinity chromatography using a second protein affixed to a solid support as an adsorbent, and
   wherein the second protein affixed to a solid support can bind to the constant antibody immunoglobulin domain.

14. The method of claim 13, wherein the recombinant fusion protein comprises an $F_c$ portion of an antibody.

15. The method of claim 13, wherein the recombinant fusion protein is TNFR:F$_c$.

16. The method of claim 13, wherein the second protein is selected from the group consisting of Protein A arid Protein G.

17. The method of claim 13, wherein hydroxyapatite chromatography is carried out in a solution comprising a sodium phosphate buffer.

18. The method of claim 17, wherein the sodium phosphate buffer is present in the solution at a concentration between about 5 millimolar and about 50 millimolar.

19. The method of claim 13, wherein hydroxyapatite chromatography is carried out at a pH between about 6.0 and about 8.6.

20. The method of claim 13, wherein, the recombinant fusion protein has been secreted into a culture medium by cultured animal cells.

21. The method, of claim 20, wherein the animal cells are CHO cells.

22. The method of claim 20, wherein at least one protein contaminant has been secreted into the culture medium byte cultured animal cells.

23. The method of claim 13 wherein:
   the recombinant fusion protein is TNFR:F$_c$;
   the second protein is Protein A or Protein G; and
   hydroxyapatite chromatography is carried out in a solution comprising a sodium phosphate buffer at a concentration between about 15 millimolar and about 35 millimolar and apH between about 6.5 and about 7.5.

24. A method for purifying TNFR:F$_c$ comprising subjecting a sample comprising TNFR:F$_c$ and at least one protein contaminant to hydroxyapatite chromatography under conditions wherein the majority of molecules of TNFR:F$_c$ are recovered in a flow through and wash, wherein ax least one protein contaminant is separated from TNFR:F$_c$.

25. A method for separating a protein from host cell proteins comprising subjecting a sample comprising the protein and at least one host cell protein to hydroxyapatite chromatography,
   whereby at least one host cell protein is separated from the protein,
   wherein the protein comprises a constant antibody immunoglobulin domain,
   wherein the majority of molecules of the protein are recovered in a flow through and wash, and
   wherein both the protein and the host cell protein have been secreted into a culture medium by cultured animal cells.

26. The method of claim 25, wherein the concentration of the host cell proteins relative to the protein in the flow through and wash is less than about 100 parts per million.

27. The method of claim 25, wherein the protein is TNFR:F$_c$.

* * * * *